(12) United States Patent
Ficko

(10) Patent No.: US 10,758,475 B2
(45) Date of Patent: Sep. 1, 2020

(54) SUN BLOCK FORMULATION

(71) Applicant: Majda Ficko, East St. Paul (CA)

(72) Inventor: Majda Ficko, East St. Paul (CA)

(*) Notice: Subject to any disclaimer, the term of this patent is extended or adjusted under 35 U.S.C. 154(b) by 0 days.

(21) Appl. No.: 16/777,347

(22) Filed: Jan. 30, 2020

(65) Prior Publication Data
US 2020/0237646 A1 Jul. 30, 2020

Related U.S. Application Data

(62) Division of application No. 16/301,128, filed as application No. PCT/CA2017/050679 on Jun. 5, 2017.

(60) Provisional application No. 62/347,338, filed on Jun. 8, 2016.

(51) Int. Cl.
| | | |
|---|---|---|
| *A61K 8/37* | (2006.01) | |
| *A61K 8/31* | (2006.01) | |
| *A61K 8/27* | (2006.01) | |
| *A61K 8/29* | (2006.01) | |
| *A61K 8/92* | (2006.01) | |
| *A61K 8/9789* | (2017.01) | |
| *A61Q 17/02* | (2006.01) | |
| *A61Q 17/04* | (2006.01) | |
| *A61K 8/9794* | (2017.01) | |

(52) U.S. Cl.
CPC ............. *A61K 8/9789* (2017.08); *A61K 8/27* (2013.01); *A61K 8/29* (2013.01); *A61K 8/31* (2013.01); *A61K 8/375* (2013.01); *A61K 8/92* (2013.01); *A61K 8/922* (2013.01); *A61K 8/927* (2013.01); *A61K 8/9794* (2017.08); *A61Q 17/02* (2013.01); *A61Q 17/04* (2013.01); *A61K 2800/43* (2013.01); *A61K 2800/805* (2013.01)

(58) Field of Classification Search
None
See application file for complete search history.

(56) References Cited

FOREIGN PATENT DOCUMENTS

WO   WO-2006010214 A1 * 2/2006 ............... A61K 8/27

* cited by examiner

*Primary Examiner* — Kyung S Chang
(74) *Attorney, Agent, or Firm* — Michael R. Williams; Ryan W. Dupuis; Ade & Company Inc.

(57) ABSTRACT

Described herein is a natural, mineral sunscreen that combines natural oxides with high linoleic acid natural oils. The result is a safe, natural formula for the whole family which is naturally tinted and made from natural ingredients. The composition has an SPF rating of 50+ and provides broad spectrum UVA and UVB protection. The composition contains powerful anti-oxidants, no artificial fragrance(s), is hypoallergenic and is safe for sensitive skin.

5 Claims, No Drawings

SUN BLOCK FORMULATION

PRIOR APPLICATION INFORMATION

The instant application is a divisional application of U.S. Ser. No. 16/301,128, filed Nov. 13, 2018, which was a 371 of PCT Application CA2017/050679, filed Jun. 15, 2017, now abandoned, which claimed the benefit of U.S. Provisional Patent Application, filed Jun. 8, 2016, under Ser. No. 62/347,338, entitled "Sun Block Formulation", the contents of which are incorporated herein by reference.

BACKGROUND OF THE INVENTION

Sunscreens and sunblocks are products that help prevent ultraviolet (UV) radiation from the sun from reaching and damaging the skin.

Ultraviolet A (UVA) refers to the longer wave UV rays that cause lasting skin damage, skin aging and can promote the development of skin cancer. Ultraviolet B (UVB) refers to the shorter wave UV rays that cause sunburns, skin damage and can promote the development of skin cancer.

Broad-spectrum products provide protection against both UVA and UVB rays.

Sun Protection Factor or SPF is a measure of a sunscreen's or sunblock's ability to prevent UVB from damaging the skin. For example, if it takes approximately 20 minutes for a person's skin to start to visibly burn, using a product with an SPF of 15 will provide 20 minutes (unprotected)×15 SPF, or 300 minutes (5 hours) of protection.

However, many sunscreens that offer broad UV protection and high SPF are either unstable or lack a suitable or desirable cosmetic finish. For example, the sunscreen can dry the skin, can feel heavy on the skin or leave a residue behind or may include compounds to which the user's skin reacts adversely, leading to irritation, rashes and/or other skin ailments.

Specifically, many chemical sunscreens contain one or more potentially harmful chemical actives.

For example, oxybenzone is known to penetrate the skin and can act like estrogen in the body. Oxybenzone can also trigger allergic skin reactions.

Homosalate is a weak hormone disruptor which can be broken down by exposure to sunlight into potentially harmful by-products.

Octinoxate has been shown to have hormone-mimicking effects on laboratory animals.

Retinyl palmitate has been shown to speed the development of skin tumors and lesions on sun-exposed skin.

As will be apparent to one of skill in the art, a sunscreen which lacks a desirable "skin feel" may not be applied frequently enough and/or to a sufficient degree for proper protection to be attained. Furthermore, sunscreens that focus on skin feel may lack sufficient UV protection An all-natural ingredient product which provides excellent sunblocking activity and also promotes and supports skin health is needed.

SUMMARY OF THE INVENTION

According to a first aspect of the invention, there is provided a sun block formulation comprises the following formula:
  20-80% (w/w) high linoleic acid natural oils;
  5-25% (w/w) zinc oxide, titanium dioxide or mixture thereof;
  0.5-15.0% (w/w) Candelilla wax; Carnauba wax; Sunflower seed wax; Beeswax; polyglyceryl-3 beeswax; carnauba wax, chuan wax, microcrystalline wax; glyceryl behenate; glyceryl behenate/eicosadioate or a mixture thereof; and
  0.5-15.0% (w/w) rice bran wax, carnauba wax, chuan wax or a mixture thereof.

The high linoleic acid natural oil may be a natural oil that has a linoleic content of approximately 60% or greater, for example, safflower oil, grape seed oil, poppyseed oil, sunflower oil, hemp oil or corn oil.

In some embodiments, the formula comprises:
  20-80% (w/w) safflower oil, grape seed oil, poppyseed oil, sunflower oil, hemp oil, corn oil or a mixture thereof;
  5-25% (w/w) zinc oxide, titanium dioxide or mixture thereof;
  0.5-15.0% (w/w) Candelilla wax; Carnauba wax; Sunflower seed wax; Beeswax; polyglyceryl-3 beeswax; carnauba wax, chuan wax, microcrystalline wax; glyceryl behenate; glyceryl behenate/eicosadioate or a mixture thereof; and
  0.5-15.0% (w/w) rice bran wax.

In other embodiments, the formula comprises:
  20-80% (w/w) safflower oil, grape seed oil, poppyseed oil, sunflower oil, or a mixture thereof
  5-25% (w/w) zinc oxide, titanium dioxide or mixture thereof;
  0.5-15.0% (w/w) Candelilla wax; Carnauba wax; Sunflower seed wax; Beeswax; polyglyceryl-3 beeswax; carnauba wax, chuan wax, microcrystalline wax; glyceryl behenate; glyceryl behenate/eicosadioate or a mixture thereof; and
  0.5-15.0% (w/w) rice bran wax.

In yet other embodiments, the formula comprises
  10-40% (w/w) Grape seed Oil;
  10-40% (w/w) Safflower Oil;
  10-25% (w/w) Zinc Oxide, titanium dioxide or a mixture thereof;
  2-40% (w/w) Emulsifier;
  1-15% (w/w) Candelilla wax;
  1-15% (w/w) Rice Bran wax;
  0.2-0.4% (w/w) anti-oxidant source;
  0.05-0.2% (w/w) coloring agent;
  0.05-0.2% (w/w) insect repelling agent;
  0.04-0.1% (w/w) antiseptic agent;

In a preferred embodiment, the formula consists of:
  34.9% (w/w) Grape seed Oil;
  32.105% (w/w) Safflower Oil;
  24.5% (w/w) Zinc Oxide;
  4% (w/w) Beeswax;
  2% (w/w) Candelilla wax;
  2% (w/w) Rice Bran wax;
  0.2% (w/w) Green Tea Powder;
  0.1% (w/w) Red2 Pigment;
  0.15% (w/w) Lavender Extract Oil;
  0.045% (w/w) Rosemary Extract Oil.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein is a sun block formulation or composition comprising all natural ingredients. As discussed herein, the formulation is a broad spectrum product and provides an SPF of 50+.

In many embodiments, the composition has no perfumes and is hypoallergenic. The composition is safe for application to sensitive skin.

As will be apparent to one of skill in the art, "sensitive skin" refers to skin that easily or frequently breaks out in rashes and/or gets blotchy or itchy or experiences a stinging sensation in response to certain stimuli, such as, for example, application of certain products to the skin. It is important to note however that even people who do not consider themselves to have sensitive skin can react adversely to the application of certain chemicals and/or compounds.

As discussed herein, the composition includes natural sources of linoleic acid and anti-oxidants. Linoleic acid is involved in the synthesis of tissue lipids and provides healing support and moisturizing to skin. Essential fatty acids such as linoleic acid are also believed to facilitate the penetration of anti-oxidants, which have been shown in vitro to inhibit formation of free radicals which are associated with skin damage in vivo.

In an embodiment of the invention, the sun block formulation comprises the following formula:

20-80% (w/w) high linoleic acid natural oils;
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax, chuan wax, microcrystalline wax; glyceryl behenate; glyceryl behenate/eicosadioate or a mixture thereof; and
0.5-15.0% (w/w) rice bran wax, carnauba wax, chuan wax or a mixture thereof.

In all formulae recited herein, the percentages are expressed on a weight/weight basis.

In some embodiments, the sunscreen formulation comprises:

20-80% (w/w) high linoleic acid natural oils;
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-15.0% (w/w) rice bran wax, carnauba wax, chuan wax or mixture thereof, with the proviso that no water is added to the formulation.

As used herein, "high linoleic acid natural oil" refers to a natural oil that has a linoleic content of approximately 60% or greater. For example, such oils include but are by no means limited to safflower oil, grape seed oil, poppyseed oil, sunflower oil, hemp oil and corn oil.

According to another aspect of the invention, there is provided a sunscreen formulation comprising:

20-80% (w/w) safflower oil, grape seed oil, poppyseed oil, sunflower oil, hemp oil, corn oil or a mixture thereof;
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate; or a mixture thereof; and
0.5-15.0% (w/w) rice bran wax.

In some embodiments, the sunscreen formulation comprises:

20-80% (w/w) safflower oil, grape seed oil, poppyseed oil, sunflower oil, hemp oil, corn oil or a mixture thereof
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-15.0% (w/w) rice bran wax, with the proviso that no water is added to the formulation.

According to another aspect of the invention, there is provided a sunscreen formulation comprising:

20-80% (w/w) safflower oil, grape seed oil, poppyseed oil, sunflower oil, or a mixture thereof;
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-15.0% (w/w) rice bran wax.

In some embodiments, the sunscreen formulation comprises:

20-80% (w/w) safflower oil, grape seed oil, poppyseed oil, sunflower oil, or a mixture thereof
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-15.0% (w/w) rice bran wax, with the proviso that no water is added to the formulation.

According to another aspect of the invention, there is provided a sunscreen formulation comprising:

20-80% (w/w) safflower oil, grape seed oil, poppyseed oil, sunflower oil, or a mixture thereof;
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-4.0% (w/w) rice bran wax.

In some embodiments, the sunscreen formulation comprises:

20-80% (w/w) safflower oil, grape seed oil, poppyseed oil, sunflower oil, or a mixture thereof
5-25% (w/w) zinc oxide, titanium dioxide or mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-4.0% (w/w) rice bran wax, with the proviso that no water is added to the formulation.

As will be known to those of skill in the art, zinc oxide is traditionally considered difficult to work with, as prior art products containing zinc oxide typically clump and are hard to spread. Furthermore, many prior art natural/physical sunscreen products have the limitation that the ingredients separate which makes them unusable/unsaleable after a short period of time. Thus, the product's overall effectiveness will be lower due to difficulties in application as a result of either clumping or separation.

In contrast, the inventor has developed a product in which the rice bran wax maintains the stability and integrity of the product and has developed a manufacturing process with an optimized "tubing" or aliquoting temperature which results in a product that spreads easily when distributed from the tube. As such, the inventor has discovered that the surprising combination of rice bran wax and a "tubing" temperature between 28-33C produces a final product that has long-term stability and excellent properties during application, thereby overcoming the limitations of many prior art natural products.

In some embodiments, the sun block composition or formulation may further include a coloring agent. As will be appreciated by one of skill in the art, the addition of a coloring agent reduces the risk that the composition will not be applied to certain regions of exposed skin as the user can clearly identify to which regions the formulation has been applied.

In some embodiments, the sun block composition further includes an emulsifier, preferably a natural emulsifier. In some embodiments, the emulsifier is beeswax.

Grape seed oil is an antioxidant-rich oil cold-pressed from grape seeds, sometimes referred to as "the perfect oil for the babies' skin". It is a favored oil for massage blends because of its light texture, and lack of colour and odour. It is one of the highest sources of polyunsaturated fatty acids.

Safflower oil has the highest linoleic acid content of all vegetable oils. Safflower oil has superior skin compatibility.

Extracted from the oil of safflower seeds, the oil is a potent hydrator and ideal for dry, sensitive complexions Safflower oil contains lubricant properties that prompt the skin to retain water and moisture. Safflower oil prevents dryness and roughness of the skin and is often used in products for the treatment of skin conditions such as eczema, psoriasis and acne. Its hydrating properties lend skin a healthy glow, promote elasticity, reduce the appearance of wrinkles and has occlusive properties.

Occurring in nature as zincite, zinc oxide is a water-insoluble substance that makes an excellent sunblock, protecting skin from UVA and UVB rays. It is a naturally occurring mineral that deflects the sun's burning rays off the skin, offering significant protection from damaging UVA/UVB rays.

Candelilla wax is extracted from *Euphorbia cerifera*, a shrub native to Mexico and is an effective emollient with extraordinary protecting properties. Candelilla Wax has a moderate melting range, good gloss, durable film and a low coefficient of contraction.

Properties such as chemical stability, water repellency, and high melting point make Candelilla useful in liquid, paste and waterproofing compounds.

It is also used as a thickening agent, an emollient and a film forming agent enabling water-repellence. The film forming properties of Candellia wax offer the possibility to use it as a fixative for UV filters in products. For this invention, Candellia wax was primarily chosen for the water repellence and UV filtering properties.

Rice bran wax is the vegetable wax extracted from the bran oil of rice. It is used as an emollient and thickener.

Specifically, Rice Bran Wax is obtained through the cold press de-waxing of rice oil which yields a yellow, hard natural wax with a high melt point.

Rice Bran Wax is a superior binder of oils and has been useful in combining with and stabilizing oils in both anhydrous and emulsion systems. It is seen as particularly effective in reducing syneresis in oil-based systems.

Rice Bran Wax is compatible with most vegetable and mineral waxes, as well as vegetable oils, mineral oils and petrolatums.

Previously, the inventor had used only Candelilla wax in the formulation and experimented with different formulae in the effort to find one that would not separate.

When sunscreen formulations separate what usually comes out first is the water and oils (liquid portion of the formula) and followed behind will be the waxes and mineral compositions, that is, the thicker ingredients. Depending on the formulation, separation can be seen in less than 3 months post-packaging.

When the product separates the oils will become rancid and unsafe for use. The liquid ingredients or oils will come to the top and separate from the thicker more stable ingredients. When the oils separate they will become oxidized or effectively rancid. It leads to the formation of free radicals and advanced lipid oxidation end products (ALEs), which are chemicals that are toxic and damaging to cells. Furthermore, the thicker ingredients may become discolored and difficult to dispense out of tube or apply to skin.

After much experimentation, the inventor found that prevention of separation was possible, but only after a high percentage of Candelilla wax was used. Specifically, from 0.5% to 4.0% resulted in separation of the product. While separation stopped at 4.0%, this formulation was too thick and could not be squeezed through a tube. It was decided to instead store the product in a jar; however, it was found that this developed a hard surface after repeated exposure to the air (opening the lid)

Surprisingly, the inventor found that when Rice Bran Wax was used in combination with the Candelilla wax, the formulation became stable. Specifically, the formulation did not separate and became easy to squeeze out of a tube and easy to apply to skin.

Specifically, the formulation has a smooth creamy texture making it easy to squeeze from a tube and apply to the skin While not wishing to be bound to a particular theory or hypothesis, it is believed that Candelilla wax is rich in nutrients and easily absorbed into the skin, allowing it to act as a barrier and help prevent moisture loss. It also works to bind ingredients together, whilst creating a workable texture. This means that it can be used to stiffen the texture of products without making them hard or it can be used as an emulsifier to prevent oil and water components from separating in products with a creamy consistency. Rice Bran Wax has similar properties to Carnauba wax and Chuan wax, but is a superior emulsifier of oils and acts as a binder. Rice Bran wax when combined with Candelilla wax helped form the stability and the creamy texture needed to be able to be squeezed out of a tube and easily applied to the skin.

In a preferred embodiment, the sun block formulation comprises the following formula:
10-40% (w/w) Grape seed Oil
10-40% (w/w) Safflower Oil
10-25% (w/w) Zinc Oxide, titanium dioxide or a mixture thereof
2-40% (w/w) Emulsifier 1-15% (w/w) Candelilla wax
1-15% (w/w) Rice Bran wax
0.2-0.4% (w/w) anti-oxidant source
0.05-0.2% (w/w) coloring agent
0.05-0.2% (w/w) insect repelling agent
0.04-0.1% (w/w) antiseptic agent.

In a preferred embodiment, the sun block formulation comprises the following formula:
10-40% (w/w) Grape seed Oil
10-40% (w/w) Safflower Oil
10-25% (w/w) Zinc Oxide, titanium dioxide or a mixture thereof
2-40% (w/w) Emulsifier
1-4% (w/w) Candelilla wax
1-4% (w/w) Rice Bran wax
0.2-0.4% (w/w) anti-oxidant source
0.05-0.2% (w/w) coloring agent
0.05-0.2% (w/w) insect repelling agent
0.04-0.1% (w/w) antiseptic agent In some embodiments, the anti-oxidant source is green tea. Green tea is a powerful antioxidant, being 20 times stronger than vitamin E (alpha tocopherol). Antioxidants such as green tea inhibit the formation of cancer-causing free radicals and help prevent skin cell damage caused by sun exposure and pollution. An anti-inflammatory and anti-irritant, green tea is high in xanthines, and is very soothing and moisturizing to skin.

In some embodiments, the emulsifier is beeswax. Beeswax is a wax secreted by honey bees. Beeswax is typically used as a natural thickener and emulsifier. Beeswax also acts as a barrier agent that locks in skin's natural moisture.

In some embodiments, the insect repelling agent is selected from Citronella oil, Clove oil, Lemongrass oil, Rosemary oil, Tea Tree oil, *Eucalyptus* oil, Cedar oil, Catnip oil, Mint oil, and lavender essential oil. In some embodiments, the insect repelling oil is lavender essential oil. Lavender essential oil is a potent repellant for many types of bugs like mosquitoes, midges, and moths and has anti-inflammatory qualities that will reduce the irritation and the pain associated with bug bites.

In some embodiments, the antiseptic agent is selected from Cinnamon Essential Oil, Geranium oil, Clove oil, and rosemary essential oil. In a preferred embodiment, the antiseptic agent is rosemary essential oil. Rosemary essential oil has antimicrobial and antiseptic qualities that make it beneficial for skin. Topical application of the essential oil helps in toning the skin and removing dryness. It can also give the skin a healthy, even glow.

In some embodiments, the coloring agent is Red2 pigment, which is Hematite/iron oxide. This mineral is used as a coloring agent in cosmetic products. Hematite varies in color from reddish-brown to black. (as an example, calamine lotion contains Zinc Oxide and a small amount of iron oxide to give a pink product)

In a preferred embodiment, the sun block formulation comprises the following formula:
34.9% (w/w) Grape seed Oil
32.105% (w/w) Safflower Oil
24.5% (w/w) Zinc Oxide
4% (w/w) Beeswax
2% (w/w) Candelilla wax
2% (w/w) Rice Bran wax
0.2% (w/w) Green Tea Powder
0.1% (w/w) Red2 Pigment
0.15% (w/w) Lavender Extract Oil
0.045% (w/w) Rosemary Extract Oil For use, the high linoleic acid natural oils are mixed with the waxes. The mixture is then heated to a temperature suitable for melting of the waxes, for example, 75° C. Once the waxes have melted the oxide source is then added while mixing until the oxide is completely dissolved in the mixture. The coloring agent may then be added and the mixture is mixed until the pigment is approximately evenly distributed throughout the mixture. At this point, heating is discontinued and mixing continues until the mixture reaches a temperature below 40° C. At that point, the essential oils, for example, Citronella oil, Clove oil, Lemongrass oil, Rosemary oil, Tea Tree oil, *Eucalyptus* oil, Cedar oil, Catnip oil, Mint oil, and/or lavender essential oil, as discussed above, are added.

In some embodiments, the mixture is distributed or aliquoted or "tubed" at a temperature of between 25 C-33 C, for example, 26 C-33 C, 27 C-33 C, 28 C-33 C, 29 C-33 C, 30 C-33 C, 31 C-33 C, 32 C-33 C, 25 C-32 C, 26 C-32 C, 27 C-32 C, 28 C-32 C, 29 C-32 C, 30 C-32 C, 31 C-32 C or about 32 C.

Specifically, it has been found that surprisingly at room temperature, the product, that is, the final mixture, is extremely fluid. Consequently, the product easily pours out of the tube and feels watery on the skin. Furthermore, when aliquoted at 34 C, the product clumps up inside the tube which makes it difficult for the product to be distributed out of the tube. Furthermore, the product does not spread nicely or smoothly on the skin. However, when the product is aliquoted at a temperature between 25-33 C, or between 28 C-33 C or between 30-33 C or about 32 degrees, the texture of the product when distributed from the tube is smooth and of the desired texture. Furthermore, the product can be squeezed easily out of the tube and spreads nicely on the skin.

The resulting product has a smooth creamy consistency, and is easily squeezed out of a tube.

According to an aspect of the invention, there is provided a method of preparing a sun block product comprising:
  mixing:
  20-80% (w/w) high linoleic acid natural oils;
  0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
  0.5-15.0% (w/w) rice bran wax, carnauba wax, chuan wax or mixture thereof, thereby producing a mixture;
  heating the mixture to about 75 C;
  adding 5-25% (w/w) zinc oxide, titanium dioxide or mixture thereof to the mixture; and
  cooling the mixture.

In some embodiments, the mixture is cooled to a temperature between 25-33 C, or between 28 C-33 C or between 30-33 C or about 32 degrees and aliquoted or distributed into tubes.

According to an aspect of the invention, there is provided a method of preparing a sun block product comprising:
  mixing:
  20-80% (w/w) safflower oil, grape seed oil, poppyseed oil, sunflower oil, hemp oil, corn oil or a mixture thereof;
  0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
  0.5-15.0% (w/w) rice bran wax, thereby producing a mixture; heating the mixture to about 75 C;

adding 5-25% (w/w) zinc oxide, titanium dioxide or mixture thereof to the mixture; and cooling the mixture.

In some embodiments, the mixture is cooled to a temperature between 25-33 C, or between 28 C-33 C or between 30-33 C or about 32 degrees and aliquoted or distributed into tubes.

According to an aspect of the invention, there is provided a method of preparing a sun block product comprising:

mixing:
20-80% (w/w) safflower oil, grape seed oil, poppyseed oil, sunflower oil, or a mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-15.0% (w/w) rice bran wax, thereby producing a mixture; heating the mixture to about 75 C;
adding 5-25% (w/w) zinc oxide, titanium dioxide or mixture thereof to the mixture; and cooling the mixture.

In some embodiments, the mixture is cooled to a temperature between 25-33 C, or between 28 C-33 C or between 30-33 C or about 32 degrees and aliquoted or distributed into tubes.

According to an aspect of the invention, there is provided a method of preparing a sun block product comprising:

mixing:
20-80% (w/w) safflower oil, grape seed oil, poppyseed oil, sunflower oil, or a mixture thereof;
0.5-15.0% (w/w) Candelilla wax; Carnauba wax; Sunflower seed wax; Beeswax; polyglyceryl-3 beeswax; carnauba wax; chuan wax; microcrystalline wax; glyceryl behenate; glyceryl behenate/eicosadioate or a mixture thereof; and
0.5-4.0% (w/w) rice bran wax; heating the mixture to about 75 C;
adding 5-25% (w/w) zinc oxide, titanium dioxide or mixture thereof to the mixture; and cooling the mixture.

In some embodiments, the mixture is cooled to a temperature between 25-33 C, or between 28 C-33 C or between 30-33 C or about 32 degrees and aliquoted or distributed into tubes.

In some embodiments, the mixture is cooled to a temperature of about 40 C prior to aliquoting and essential oils are added to the mixture, as discussed above.

For use, apply approximately 1 oz of the composition liberally and evenly to exposed skin approximately 15 minutes before sun exposure; however, the product works immediately upon application. Reapply at least every 2 hours. Reapply after 80 minutes of swimming or sweating. Reapply immediately after towel drying.

The resulting product is a natural, mineral sunscreen. The result is a safe, natural formula that offers superior sunburn protection for the whole family which is naturally tinted and made from natural ingredients. The composition has an SPF rating of 50+ and provides broad spectrum UVA and UVB protection. The product is also very water resistant even after 80 minutes. The composition contains powerful anti-oxidants, no artificial fragrance(s), is hypoallergenic and is safe for sensitive skin.

A formulation comprising:
Grape seed Oil (w/w) 34.90%
Safflower Oil (w/w) 34.90%
Zinc Oxide (w/w) 24.50%
Beeswax (w/w) 4.90%
Candellilla wax (w/w) 0.50%
Green Tea Powder (w/w) 0.20%
Red 2 Pigment (w/w) 0.10%
was tested to determine SPF and for broad spectrum UV protection.

Specifically, the sun protection factor determination test was carried out as defined by the FDA Sunscreen Final Rule: 21 CFR Parts 201 and 310 [Docket No. FDA-1978-N-0018] using a Xenon arc solar simulator as the UV source. This test was conducted prior to and immediately following an 80 minute water immersion experiment which was carried out prior to and immediately following an 80 minute water immersion experiment.

10 test subjects from 20-59 years were used in the test. One test subject had Type I skin (always burns easily, never tans); 7 test subjects had Type II skin (always burns easily; tans minimally); and 1 test subject had Type III skin (burns moderately; tans gradually).

The results of the test showed that the formulation provided an SPF of between 51.00 to 58.65 for all subjects, regardless of skin type.

The formulation was also subjected to a continuous emission spectrum from 290 to 400 nm with a limit of 1500 $W/m^2$ on total solar simulator irradiance for all wavelengths between 250 and 1400 nm. The following percentages of erythema-effective radiation in each specified range of wavelengths was obtained:

| Wavelength Range (nm) | Erythemal Contribution (%) |
|---|---|
| <290 | <0.1 |
| 290-300 | 1.0-8.0 |
| 290-310 | 49.0-65.0 |
| 290-320 | 85.0-90.0 |
| 290-330 | 91.5-95.5 |
| 290-340 | 94.0-97.0 |
| 290-400 | 99.9-100.0 |

The scope of the claims should not be limited by the preferred embodiments set forth in the examples but should be given the broadest interpretation consistent with the description as a whole.

The invention claimed is:

1. A sun block product comprising the following formula:
20-80% safflower oil, grape seed oil, poppyseed oil, sunflower oil, hemp oil, corn oil or a mixture thereof;
5-25% zinc oxide, titanium dioxide or mixture thereof;
0.5-15.0% Candelilla wax; Beeswax; polyglyceryl-3 beeswax; or a mixture thereof; and
0.5-15.0% rice bran wax,
wherein the obtained sun block product has a creamy texture and is stable without ingredient separation and the creamy texture is soft to be squeezed out of a tube, compared to a sun block product without the rice bran wax.

2. The sun block product according to claim 1 wherein the formula comprises:
0.5-4.0% rice bran wax.

3. The sun block product according to claim 1 wherein the formula comprises 10-40% grape seed oil; 10-40% safflower oil; 10-25% zinc oxide, titanium dioxide or a mixture thereof; 2-40% emulsifier; 1-15% candelilla wax; and 1-15% rice bran wax, and wherein the formula further comprises 0.2-0.4% anti-oxidant source; 0.05-0.2% coloring agent; 0.05-0.2% insect repelling agent; and 0.04-0.1% antiseptic agent.

4. The sun block product according to claim 3 wherein the formula comprises
- 10-40% Grape seed Oil;
- 10-40% Safflower Oil;
- 10-25% Zinc Oxide, titanium dioxide or a mixture thereof;
- 2-40% Emulsifier;
- 1-4% Candelilla wax;
- 1-4% Rice Bran wax;
- 0.2-0.4% anti-oxidant source;
- 0.05-0.2% coloring agent;
- 0.05-0.2% insect repelling agent; and
- 0.04-0.1% antiseptic agent.

5. The sunblock product according to claim 3 wherein the formula comprises
- 34.9% Grape seed Oil;
- 32.105% Safflower Oil;
- 24.5% Zinc Oxide;
- 4% Beeswax;
- 2% Candelilla wax;
- 2% Rice Bran wax;
- 0.2% Green Tea Powder;
- 0.1% Red2 Pigment;
- 0.15% Lavender Extract Oil; and
- 0.045% Rosemary Extract Oil.

* * * * *